United States Patent [19]
Wang et al.

[11] Patent Number: 6,011,186
[45] Date of Patent: Jan. 4, 2000

[54] PROCESS FOR MANUFACTURING ALLYLHALIDE AND EQUIPMENT TO BE USED THEREFOR

[75] Inventors: Hongwei Wang; Jacob Peenstra; Paulus Johannes Maria Rek; Petrus Joannes Josephus Tromp; Arian Van Mourik, all of Amsterdam, Netherlands

[73] Assignee: Shell Oil Company, Houston, Tex.

[21] Appl. No.: 09/067,373

[22] Filed: Apr. 27, 1998

[51] Int. Cl.[7] ........................... C07C 17/10; C07C 17/02
[52] U.S. Cl. ........................................... 570/234; 570/153
[58] Field of Search ..................................... 570/153, 234

[56] References Cited

U.S. PATENT DOCUMENTS

| | | |
|---|---|---|
| 2,763,699 | 9/1956 | Van Dijk et al. . |
| 4,590,044 | 5/1986 | Mos et al. . |
| 5,367,105 | 11/1994 | Miyazaki et al. ........................ 570/234 |
| 5,504,266 | 4/1996 | Tirtowidjojo et al. ................... 570/234 |

FOREIGN PATENT DOCUMENTS

| | | |
|---|---|---|
| 0107215 | 5/1984 | European Pat. Off. . |
| 0594454 A1 | 10/1993 | European Pat. Off. . |
| 0761831 | 11/1956 | United Kingdom . |

OTHER PUBLICATIONS

Patent Abstract of Japan, vol. 10, No. 199 (C–359), Jul. 11, 1986, JP–61/040,232 (Sumitomo Chem. Co. Ltd.) Feb. 26, 1986.

Chemical Abstracts, vol. 079, No. 23, Dec. 10, 1973, Columbus, Ohio, U.S.; Abstract No. 136471 Yamamoto H. et al., JP 48/026,732.

*Primary Examiner*—Alan Siegel

[57] ABSTRACT

A process for manufacturing allylhalide from gaseous propene and a gaseous halogen comprising introducing propene into a tubular loop reactor (2) through an inlet nozzle (3); introducing gaseous halogen into the tubular loop reactor (2) through several axially spaced groups (6) of radially placed inlet openings (4); allowing the propene and the halogen to react; and removing reaction effluent from the tubular loop reactor (2) through an outlet opening (9), wherein the concentration of halogen in any reactor volume-element is maintained below 3% by mass based on the total gas mixture, and wherein the linear gas velocity of the propene exiting the inlet nozzle is at least sufficient to maintain a continuous circulation within the tubular loop reactor (2) and equipment to be used for said process.

10 Claims, 3 Drawing Sheets

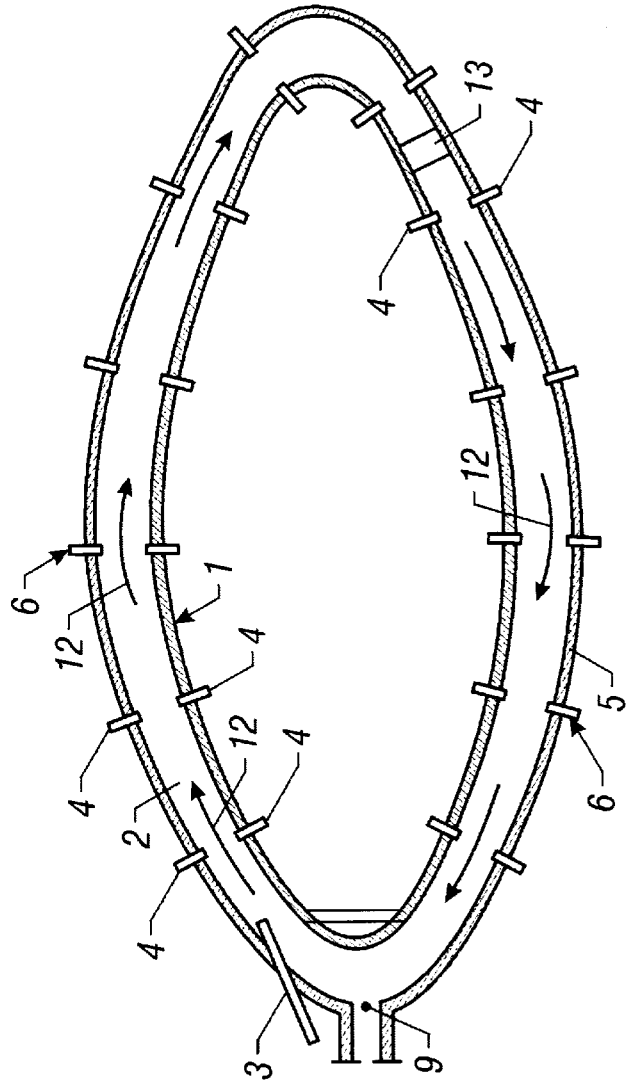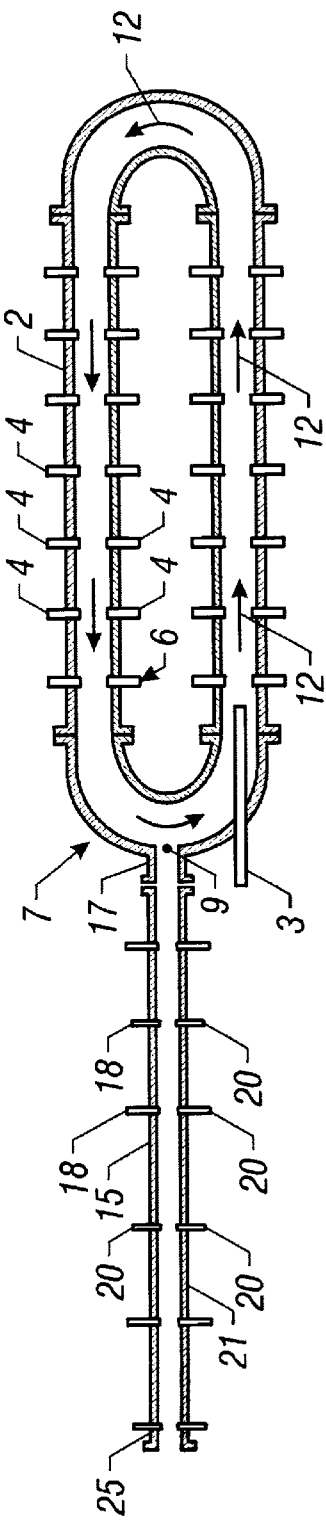
FIG. 1C
FIG. 2

PROCESS FOR MANUFACTURING ALLYLHALIDE AND EQUIPMENT TO BE USED THEREFOR

1. BACKGROUND OF THE INVENTION

The invention relates to a process for manufacturing allylhalide and a reactor which can suitably be used in such a process. More in particular the invention relates to manufacturing allylhalide by high temperature chlorinating propene in the gaseous phase.

2. BACKGROUND OF THE INVENTION

Allylhalides and more in particular allylchloride represent important intermediates for the manufacture of epihalohydrin and in particular of epichlorohydrin, which in its turn is up to now a key chemical for the manufacture of epoxy resins.

U.S. Pat. No. 5,504,266 discloses a two-stage process for manufacturing allylhalide, which process comprises:

(a) supplying propene and halogen in a molar ratio of at least 2.5:1 and suitably less than 5:1 into a continuously stirred tank reactor;

(b) allowing propene and halogen to partly react in the continuously stirred tank reactor at a temperature in the range of from 400 to 525° C. to partially convert;

(c) feeding effluent from the continuously stirred tank reactor into a pipe reactor where the reaction is allowed to continue in plug-flow at a temperature in the range of from 400 to 525° C.; and (d) removing the reaction product from the pipe reactor.

The continuously stirred tank reactor has the shape of a sphere, an oval or an egg.

U.S. Pat. No. 5,367,105 discloses a process for manufacturing allylhalide, which process comprises introducing into a reactor substantially parallel jets of gaseous propene and gaseous chlorine in a molar ratio in the range of from 3:1 to 5:1, and removing the reaction product from the reactor.

The reactor used in the above process comprises a cylindrical housing having a conical top section and an inverted conical bottom section, wherein the reactants are injected into the conical top section.

It had been found that the known processes have disadvantages, in that they either provide a relatively low yield or that a substantial amount of by-products are formed which latter products cause fouling. Moreover scaling-up the known processes was found to be difficult.

Since allylhalides are becoming increasingly more valuable, there is an incentive to improve the yield and to reduce the production of by-products.

3. SUMMARY OF THE INVENTION

As a result of intensive research an improved process has been found which suffers less from the drawbacks of the known processes.

Accordingly the process for manufacturing allylhalide from gaseous propene and a gaseous halogen according to the present invention comprises:

(a) introducing propene into a tubular loop reactor through an inlet nozzle;

(b) introducing gaseous halogen into the tubular loop reactor through several axially spaced groups of radially placed inlet openings which are provided in the wall of the tubular loop reactor;

(c) allowing the propene and the halogen to react; and (d) removing reaction effluent from the tubular loop reactor through an outlet opening, wherein the concentration of halogen in any reactor volume-element is maintained below 3% by mass based on the total gas mixture, and wherein the linear gas velocity of the propene exiting the inlet nozzle is at least sufficient to maintain a continuous circulation within the tubular loop reactor.

4. BRIEF DESCRIPTION OF THE DRAWINGS

FIGS. 1a, 1b and 1c show schematically three elongated sections of examples of reactors which can suitably be used in the process according to the invention;

FIG. 2 shows schematically a longitudinal section of an improved design of the reactor.

5. DETAILED DESCRIPTION OF THE INVENTION

In the specification and in the claims the term 'reactor volume-element' is used to refer to an element defined by the inner surface of the reactor and two axially spaced apart planes perpendicular to the direction of fluid flow through the reactor, which element has a thickness that is small compared to the inner diameter of the reactor.

The halogenation reaction is exothermic, and an advantage of the process of the present invention is that the continuous circulation provides an even temperature distribution throughout the reactor. Moreover the recirculation rate can be adjusted to improve temperature control.

According to a preferred embodiment of the process of the present invention further comprises:

(e) introducing the reaction effluent removed in step (d) in the inlet end of a pipe reactor;

(f) introducing gaseous halogen into the pipe reactor through several axially spaced groups of radially placed inlet openings which are provided in the wall of the pipe reactor, and allowing the halogen and propene to react; and (g) removing reaction product from the outlet end of the pipe reactor.

Preferably the halogen gas is chlorine gas.

The invention further relates to a reactor, comprising a tubular loop reactor provided with at least one inlet nozzle, several axially spaced groups of radially placed inlet openings which are provided in the wall of the tubular loop reactor, and an outlet opening.

Figure 1A:
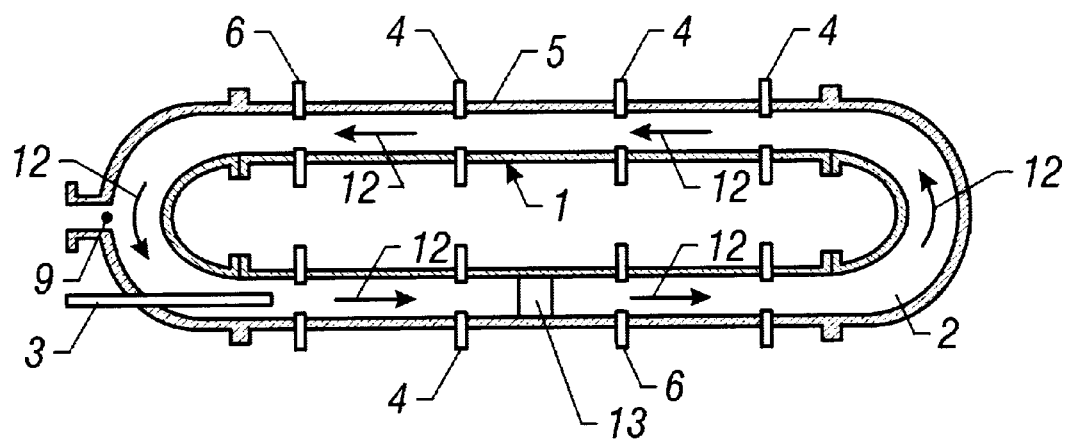
Figure 1B:
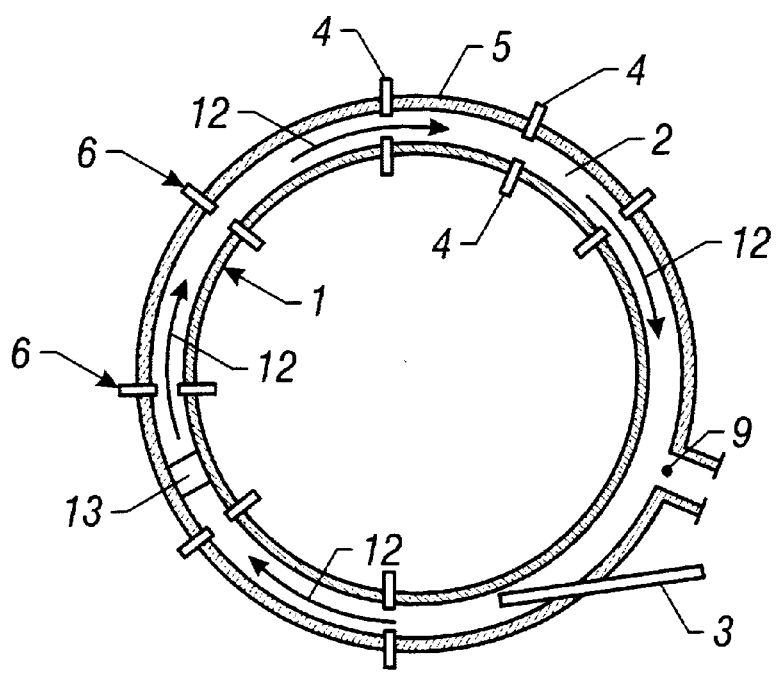
Figure 3:
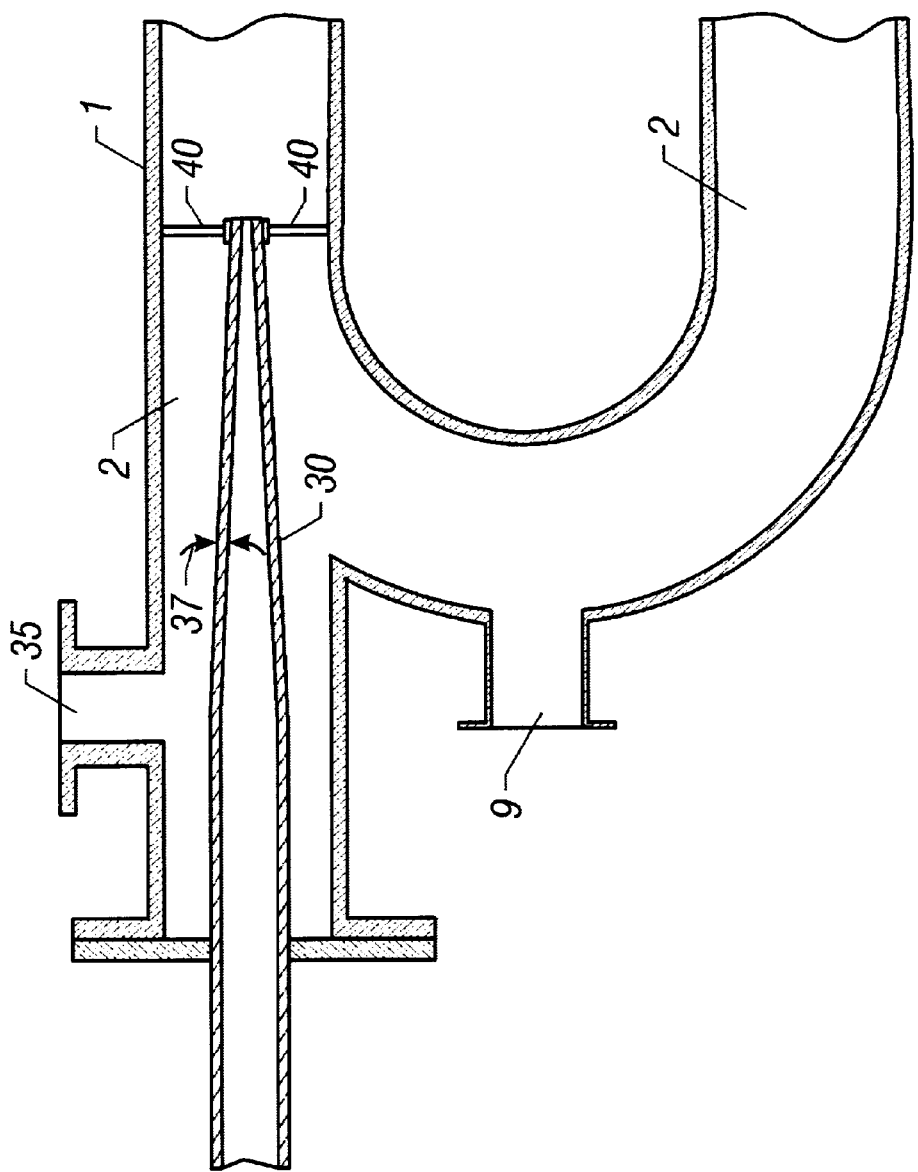
FIG. 3 shows schematically a longitudinal section of part of the tubular loop reactor drawn to a scale larger than that of FIGS. 1a–1c.

The invention will now be described by way of example in more detail with reference to the accompanying drawings, wherein FIGS. 1a, 1b and 1c show schematically three elongated sections of examples of reactors which can suitably be used in the process according to the invention;

FIG. 2 shows schematically a longitudinal section of an improved design of the reactor; and FIG. 3 shows schematically a longitudinal section of part of the tubular loop reactor drawn to a scale larger than that of FIGS. 1a–1c.

Reference is now made to FIGS. 1a–1c. The reactor 1 comprises a tubular loop reactor 2. The tubular loop reactor 2 can have an elongated shape (as shown in FIG. 1a), a circular shape (as shown in FIG. 1b) or an elliptical shape (as shown in FIG. 1c).

The tubular loop reactor 2 is provided with at least one inlet nozzle 3 and a plurality of inlet openings 4 which are provided in the wall 5 of the tubular loop reactor 2. The inlet openings 4 are arranged in several axially spaced groups 6, and in each group the inlet openings are radially placed, that is to say distributed along the circumference of the tubular loop reactor 2. For the sake of clarity, not all inlet nozzles and not all groups have been referred to with reference numerals.

The tubular loop reactor is furthermore provided with an outlet opening 9 arranged near the inlet nozzle 3. Suitably, the outlet opening 9 is located at the downstream end of the tubular loop reactor 2, downstream of the inlet nozzle 3.

During normal operation, propene is introduced into the tubular loop reactor 2 through the inlet nozzle 3, and gaseous halogen is introduced into the tubular loop reactor 2 through the plurality of inlet openings 4. The reaction mixture passes through the tubular loop reactor 2 in the direction of the arrows 12. Reaction effluent is removed from the tubular loop reactor 2 through the outlet opening 9, and from there the reaction effluent is passed to a recovery equipment (not shown) to isolate the desired allylhalide by methods known per se. The remainder of the reaction effluent circulates through the tubular loop reactor 2. The recycle ratio (R) is defined as the mass ratio of the amount of recirculated reaction mixture to the amount of propene injected by the injection nozzle 3.

The conditions are so selected that the concentration of halogen in any reactor volume-element 13 is maintained below 3% by mass based on the total gas mixture, and the linear gas velocity of the propene exiting the inlet nozzle 3 is at least sufficient to maintain a continuous circulation within the tubular loop reactor 2.

The linear gas velocity ($U_{propene}$) of the propene leaving the inlet nozzle(s) must be sufficient to give rise to:
a) an average velocity ($U_{loop}$) in each cross-section of the tubular loop reactor above 20 m/s, preferably above 40 m/s; and
b) a recycle ratio (R) that ensures the minimum temperature in the loop reactor above 400° C., preferably above 430° C. The maximum temperature in the loop reactor must be below 520° C., preferably below 500° C.

Suitable values for the recycle ratio (R) are greater than 2 and preferably more than 3.

Applicant had found that when so selecting the conditions, allylhalide and preferably allylchloride can be produced with good selectivity. Due to the significant reduction of by-products, and in particular 1,5-hexadiene which is the main precursor for heavy chloroethers in the effluent, the obtained allylchloride is less coloured.

Suitably the number of groups 6 of inlet openings 4 is in the range of from 2 to 15 and preferably in the range of from 6 to 12, and the number of inlet openings 4 per group is in the range of from 2 to 8.

The number of radially placed halogen inlet openings per group in one cross-section is normally in the range of from 2 to 15 and preferably from 4 to 12.

Suitably there is more than one injection nozzle 3, which injection nozzles are axially spaced apart along the tubular loop reactor 2. For determining the recycle ratio, the total amount of propene from all injection nozzles is taken.

Reference is now made to FIG. 2. The reactor 1 shown in this Figure further comprises a pipe reactor 15, having an inlet end 17 which is in fluid communication with the outlet opening 9 of the tubular loop reactor 2.

The pipe reactor 15 is provided with several axially spaced groups 19 of radially placed inlet openings 20 which are provided in the wall 21 of the pipe reactor 15.

The pipe reactor 15 has an outlet end 25 for removing the reaction product from the reactor 1.

During normal operation, the reaction effluent removed from the outlet opening 9 is introduced into the inlet end 17 of the pipe reactor 15, gaseous halogen is introduced into the pipe reactor 15 through the axially spaced groups 19 of radially placed inlet openings 20 which are provided in the wall of the pipe reactor. The halogen is allowed to react with unreacted propene, and the reaction product is removed from the outlet end 25 of the pipe reactor 15, and from there the reaction product is passed to a recovery equipment (not shown) to isolate the desired allylhalide by methods known per se.

Reference is now made to FIG. 3. The inlet nozzle used in this design is an ejector 30, and part of the propene feed can be introduced through auxiliary inlet 35, so that the recycle ratio can be reduced by adjusting the amounts of propene supplied through the ejector 30 and through the auxiliary inlet 35. As shown in FIG. 3, the end part of the ejector 30 is tapered, and the half top angle 37 is about 2°. Furthermore, the end of the ejector 30 is supported by support bars 40, of which there are suitably 3.

If according to a preferred embodiment of the process of the invention, a combination of a loop reactor and an interconnected pipe reactor is used the molar ratio of the halogen introduced into the tubular loop reactor relative to the total halogen introduced into both the tubular loop reactor and the pipe reactor is in the range of from 60 to 100%, and more preferably from 70 to 90%.

The inlet temperature of the halogen feed and preferably the chlorine feed is in the range of from 50 to 150° C. and preferably from 60 to 110° C. and more preferably from 80 to 110° C., while the temperature of halogen introduced via each respective inlet may be the same or different.

Preferably the temperature of the halogen and preferably the chlorine gas introduced into the tubular loop reactor will be about the same, and the temperature of the halogen gas introduced in the optional pipe reactor may have the same value too, although the respective temperatures of the halogen, introduced into the loop reactor on the one hand and into the optional pipe reactor on the other hand, may be different. The introduced propene will have a temperature in the range of from 200 to 400° C., and preferably from 230 to 360° C. Different reaction temperatures can be applied in different cross-sections of the loop reactor and the optional pipe reactor respectively and in particular in the pipe reactor sections various zones of temperatures can be applied.

Typically the residence time ($\tau_{loop}$) in the loop reactor is on average from 0.5 s to 3 s and the residence time in the pipe reactor ($\tau_{pipe}$) is from 0.2 s to 1 s.

In general, the inner diameter (in m) of the tubular loop reactor are determined by the following equation:

$$D_{loop} = A * (R/\tau_{loop}) * (U2_{propene}/U3_{loop}) * d2,$$

wherein A is an empirical depending on the surface property of the reactor material (–); R the recycle ratio (–); $\tau_{loop}$ the residence time in the loop reactor (in s); $U_{propene}$ the linear velocity of the propene exiting the nozzle (in m/s); $U_{loop}$ the linear velocity in the tubular loop reactor (in m/s); and d the inner diameter of the propene nozzle (in m).

Under practical conditions A will have a value in the range of from 20 to 40 and preferably from 25 to 35.

The number of the groups of inlet openings along the tubular loop reactor is selected to the aforementioned critical concentration requirement. It is preferable to position the groups at an equal distance along the tubular loop reactor.

The inner diameter of the pipe reactor is so selected that the linear velocity in the pipe reactor is between 20 and 80 m/s. The determination of the number of groups of inlet openings and their positions is determined in the same way as for the tubular loop reactor.

According to a preferred embodiment, using a combination of loop reactor and a pipe reactor the volume of the loop reactor is relatively large compared to the volume of the pipe reactor.

It will be appreciated that the invention also relates to a specific reactor assembly wherein the hereinbefore specified process is performed.

It will be appreciated that more preferably this pipe reactor is constituted by a straight pipe connected to the loop reactor via outlet opening, however, other alternatives, wherein the straight pipe reactor is connected to the loop reactor via one or more bent tube parts can also be applied.

More preferably the ratio of the inner diameter of the loop reactor and the inner diameter of the pipe reactor is in the range of from 4:1 to 3:2 and the ratio of the volume of the tubular loop reactor, relative to the volume of the pipe reactor is in the range of from 6 to 9.

In a reactor assembly as depicted in FIG. 2 the ratio of the external maximum length of said loop reactor relative to the diameter of the tube constituting the loop reactor is in the range of from 30 to 50, while the ratio of the external width of said tubular loop reactor relative to the diameter is in the range of from 3 to 5.

A more preferred ratio of the external maximum length of the tubular loop reactor, relative to the inner diameter of the loop reactor is in the range of from 35 to 45.

The invention is further illustrated by the following example, however without restricting its scope to this embodiment.

EXAMPLE 1

In a reactor according to FIG. 2, propene was converted with chlorine under the following conditions:

| | |
|---|---|
| Propene preheat (° C.): | 340 |
| Chlorine preheat (° C.): | 70 |
| Propene/chlorine molar ratio: | 4.2 |
| Reactor outlet temperature (° C.): | 505 |
| Propene feed rate (kg/h): | 6300 |
| Chlorine feed rate (kg/h): | 2536 |
| Reaction pressure (bara): | 3.2 |
| Residence time in the loop reactor, $\tau_{loop}$ (s): | 1.8 |
| Residence time in the pipe reactor, $\tau_{pipe}$ (s): | 0.2 |
| Linear velocity of the propene ejector, $U_{propene}$(m/s): | 355 |
| Gas velocity in the loop reactor, $U_{loop}$ (m/s): | 40 |
| Inner diameter of the loop reactor, $D_{loop}$ (m): | 0.3 |
| Inner diameter of the pipe reactor, $D_{pipe}$ (m): | 0.15 |
| Diameter of the propene ejector, d (m): | 0.055 |
| Number of chlorine inlet groups in the loop reactor: | 7 |
| Number of chlorine inlet groups in the pipe reactor: | 3 |
| Recycle ratio: | 3 |
| Yield based on moles of propene converted (mol %): | |
| Allylchloride: | 89.37 |
| 2-Chloropropene: | 2.81 |
| 1,2-Dichloropropane: | 1.38 |
| cis-1,3-Dichloropropene: | 1.95 |
| trans-1,3-Dichloropropene: | 1.76 |
| others: | 2.73 |

We claim:

1. A process for manufacturing allylhalide from gaseous propene and a gaseous halogen, comprising:

(a) introducing propene into a tubular loop reactor through an inlet nozzle;

(b) introducing gaseous halogen into the tubular loop reactor through several axially spaced groups of radially placed inlet openings which are provided in the wall of the tubular loop reactor;

(c) allowing the propene and the halogen to react; and (d) removing reaction effluent from the tubular loop reactor through an outlet opening, wherein the concentration of halogen in any reactor volume-element is maintained below 3% by mass based on the total gas mixture, and wherein the linear gas velocity of the propene exiting the inlet nozzle is at least sufficient to maintain a continuous circulation within the tubular loop reactor.

2. Process as claimed in claim 1, wherein the reaction effluent is removed from the tubular loop reactor through an outlet opening arranged near the inlet nozzle.

3. Process according to claim 1, wherein reaction in step (c) is carried out at a temperature in the range of from 430 to 520° C.

4. A process according to claim 1, wherein the halogen concentration in the gaseous reaction mixture in each reactor-volume element is maintained in the range of from 0.5 to 1.5% by mass.

5. Process according to claim 1, wherein the inlet temperature of the halogen feed is in the range of from 80 to 110° C.

6. Process according to claim 1, further comprising:

(e) introducing the reaction effluent removed in step (d) in the inlet end of a pipe reactor;

(f) introducing gaseous halogen into the pipe reactor through several axially spaced groups of radially placed inlet openings which are provided in the wall of the pipe reactor, and allowing the halogen and propene to react; and (g) removing reaction product from the outlet end of the pipe reactor.

7. A process according to claim 1, wherein the propene feed has a temperature in the range of from 200 to 400° C.

8. Process according to claim 1, wherein the residence time in the loop reactor ($\tau_{loop}$) is in the range from 0.5 s to 3 s.

9. Process according to claims 6, wherein the residence time in the pipe reactor ($\tau_{pipe}$) is in the range of from 0.2 s to 1 s.

10. Process according to claim 1, wherein the halogen is chlorine.

* * * * *